United States Patent
Hansen et al.

(10) Patent No.: US 8,815,313 B2
(45) Date of Patent: Aug. 26, 2014

(54) COMPOSITIONS OF ROSE HIPS ENRICHED WITH SEEDS OF ROSE HIPS AND THEIR USE AS ANTI-INFLAMMATORY NATURAL MEDICINE FOR ALLEVIATING/REDUCING SYMPTOMS ASSOCIATED WITH INFLAMMATION AND JOINT DISEASES SUCH AS ARTHRITIS, RHEUMATOID ARTHRITIS AND/OR OSTEO-ARTHRITIS

(75) Inventors: Otto Torbjørn Hansen, Tranekaer (DK); Arsalan Kharazmi, Hellerup (DK); Eydbjørg Winther Hansen, Hornbaek (DK)

(73) Assignee: Hyben Vital Licens ApS, Tranekaer (DK)

( * ) Notice: Subject to any disclaimer, the term of this patent is extended or adjusted under 35 U.S.C. 154(b) by 0 days.

(21) Appl. No.: 13/583,545

(22) PCT Filed: Mar. 16, 2011

(86) PCT No.: PCT/DK2011/000017
§ 371 (c)(1),
(2), (4) Date: Nov. 27, 2012

(87) PCT Pub. No.: WO2011/113433
PCT Pub. Date: Sep. 22, 2011

(65) Prior Publication Data
US 2013/0122126 A1    May 16, 2013

(30) Foreign Application Priority Data

Mar. 16, 2010 (DK) .............................. PA 2010 00209
Jul. 12, 2010 (DK) .............................. PA 2010 00616

(51) Int. Cl.
A61K 36/73 (2006.01)
A61K 36/00 (2006.01)
A61K 36/738 (2006.01)

(52) U.S. Cl.
CPC .................................... A61K 36/738 (2013.01)
USPC ........................... 424/765; 424/725; 424/776

(58) Field of Classification Search
None
See application file for complete search history.

(56) References Cited

U.S. PATENT DOCUMENTS

| 6,024,960 | A | 2/2000 | Kharazmi et al. | |
| 6,485,752 | B1 | 11/2002 | Rein et al. | |
| 7,084,122 | B2 | 8/2006 | Larsen et al. | |
| 2007/0269540 | A1* | 11/2007 | Ninomiya et al. | 424/765 |
| 2009/0209746 | A1 | 8/2009 | Bagger et al. | |
| 2011/0257110 | A1 | 10/2011 | Kharazmi et al. | |
| 2012/0128737 | A1 | 5/2012 | Oesser | |
| 2012/0184023 | A1 | 7/2012 | Bagger et al. | |

FOREIGN PATENT DOCUMENTS

| DE | 4424419 A1 | 1/1996 |
| RU | 2055483 C1 | 3/1996 |

OTHER PUBLICATIONS

Chrubasik et al, A systematic review on the Rosa canina effect and efficacy profiles. Phytotherapy research: PTR, (Jun. 2008) vol. 22, No. 6, pp. 725-733.*
International Search report for PCT/DK2011/000017, mailed May 30, 2011, 3 pages.
Danish Search Report for application PA 2010 00616, mailed Mar. 9, 2011, 2 pages.
Wenzig, E.M. et al. "Phytochemical composition and in vitro pharmacological activity of two rose hip (Rosa canina L.) preparations" Phytomedicine, vol. 15, 2008, pp. 826-835.
Vitetta, L., et al. "Alternative therapies for musculoskeletal conditions", Best Practice & Research Clinical Rheumatology, Vol, 22, No. 3, 2008, pp. 499-522.
Rossnagel, K. et al., Klinische Wirksamkeit von Hagebuttenpulver bei Patienten mit Arthroses MMW—Fortschritte der Medizin, vol. 149, 2007, pp. 51-56.
Chrubasik, C. et al., "The evidence for clinical efficacy of rose hip and seed: A systematic review", Phytotherapy Research, vol. 20, 2006, pp. 1-3.
Kharazmi, A. Laboratory and preclinical studies on the anti-inflammatory and anti-oxidant properties of rosehip powder—Identification and characterization of the active component GOPW®, Osteoarthritis and Cartilage, vol. 16, 2008, Supplement 1, pp. S5-S7.
Ninomiya, K. et al., "Potent anti-obese principle from *Rosa canina*: Structural requirements and mode of action of trans-tillroside", Bioorganic & Medicinal Chemistry Letters, vol . 1 7, 2007, pp. 3059-3064.
Kang, S.C. et al., "Effects of fructus and semen from *Rosa Rugosa* on osteoimmune cells", Korean Journal of Plant Resources, vol. 23, No. 2, 2010, pp. 157-164.

\* cited by examiner

*Primary Examiner* — Qiuwen Mi
(74) *Attorney, Agent, or Firm* — William J. Sapone; Ware Fressola Maguire & Barber LLP

(57) ABSTRACT

A composition containing rose hip flesh or rose hips including the naturally occurring amount of seeds, or a concentrate is enriched with rose hip seeds for reducing and/or alleviating symptoms of inflammatory diseases. A method of preparing the rose hip seeds involves separating the rose hip seeds from the flesh prior to or after drying. Drying is preferably performed below 50° C. with the rose hip seeds then ground into a powder and mixed with a rose hip composition, a concentrate or an extract containing rose hip shells or Rose hips including their naturally occurring amount of seeds providing a product enriched with Rose hips seeds preferably containing at least 50% up to 85%, (by weight) of rose hip seeds. The composition is useful in the prophylaxis, treatment or alleviation of symptoms related to inflammatory diseases, in particular joint diseases, such as arthritis rheumatoid arthritis and/or osteo arthritis.

34 Claims, 1 Drawing Sheet

COMPOSITIONS OF ROSE HIPS ENRICHED WITH SEEDS OF ROSE HIPS AND THEIR USE AS ANTI-INFLAMMATORY NATURAL MEDICINE FOR ALLEVIATING/REDUCING SYMPTOMS ASSOCIATED WITH INFLAMMATION AND JOINT DISEASES SUCH AS ARTHRITIS, RHEUMATOID ARTHRITIS AND/OR OSTEO-ARTHRITIS

CROSS REFERENCE TO RELATED APPLICATIONS

This application is a National Stage of PCT International Application serial number PCT/DK2011/000017, filed 16 Mar. 2011, claiming priority in Danish patent application numbers PA 2010 002909 filed 16 Mar. 2010 and PA 2010 00616 filed 12 Jul. 2010, the contents of which are hereby incorporated by reference.

FIELD OF THE INVENTION

The present invention relates to a composition based on rose hip seeds for reducing and/or, alleviating symptoms of inflammatory diseases, especially joint diseases such as rheumatoid arthritis, reactive or osteo-arthritis or other arthritides. The invention also relates to a method of preparing the rose hip seeds product and use of the rose hip seed composition in the prophylaxis, treatment or alleviation of symptoms related to inflammatory diseases, in particular joint diseases, such as arthritis and/or osteo arthritis.

BACKGROUND OF THE INVENTION

The fruit of the dog rose (*Rosa Canina* L. —Rosaceae) has been used for medical purposes for centuries. A rose hip weighs approximately 1.25-3.25 g of which approximately 70% (by weight) is flesh/pericarp, while approximately 30% is seeds. Rose hips were previously and are still mostly consumed as tea produced on the dried flesh, and was previously especially used against common cold. In the last 2 decades rose hips products have also been suggested as a herbal remedy to treat or alleviate arthritic symptoms and other inflammatory diseases and/or symptoms and other diseases/symptoms, e.g. obesity.

Osteoarthritis is characterized by an erosion of articulated cartilage which becomes soft, frayed and thinned with eburnation of subchondral bone and outgrowths of marginal osteophytes. Pain and loss of function is the result. This is more common in older persons and is considered degenerative joint disease which mainly affects the weight bearing joints such as the hips and knees.

While inflammation is one symptom of arthritis, the pain and stiffness of the joints are particularly debilitating as this physically inhibits activity and lessens the motivation for daily activities, as well as causes sleeplessness, and results in an overall negative impact on the general well being of an individual, as one susceptible to such pain and joint stiffening must generally refrain from normal daily activities such as walking, entering a vehicle, etc.

Various rose hip formulations are known and have shown different levels of anti-inflammatory effects. For example, in U.S. Pat. No. 6,024,960 A, a rose hip formulation based on the shells of rose hips for use as an anti-inflammatory natural medicine is described. The daily dose is 20-200 g of the rose hip powder, and preferably about 45 g rose hip powder.

In EP1337263 B1 it was shown that a daily administration of a rose hip concentrate based on the shells of rose hips and fish oil may be used to treat and/or alleviate the symptoms associated with joint diseases such as osteoarthritis, especially joint pain and joint stiffness.

In RU 2055483 A1 a composition containing ground seeds of rose hips in a mixture with starch and sulphur is disclosed as an additive for farm animals' feedstuff.

Wenzig et al. "Phytochemical composition and in vitro pharmacological activity of two Rose hip (*Rosa Canina* L.) preparations" Phytomedicine, vol. 15, 2008, p. 826-835 discloses an increased anti-inflammatory effect of an extract of rose hip flesh when compared to an extract of Rose hips including the seeds.

K. Winther et al.: "A powder made from seeds and shells of rose hip species (*rosa canina*) reduce symptoms of knee and hip osteoarthiritis: A randomized double blind placebo controlled clinical trial", Scand J Rheumatol, 2005, 34, 302-308 describes a clinical trial of a rose hip product containing both rose hip shells and seeds, wherein the osteoarthritis patients are treated with a daily dose of 5 g of rose hip powder. One conclusion from the study indicates that the dose of 5 g of rose hip powder daily was not optimal, indicating that the effective daily dose in fact may be larger than 5 g rose hip powder.

Szentmihalyi et al.: "Rose hip (*Rosa canina* L.) oil obtained from rose hip seeds by different extraction methods", Biores. Tech., 82, 2002, p. 195-201, describes different extraction methods for obtaining a rose hip seeds oil having a yield of 3.23 g oil per 100 g seeds to 6.68 g oil per 100 g seeds which may be useful for medical purposes.

Willich, S. N. et al: "Rose hip herbal remedy in patients with rheumatoid arthritis—a randomized controlled trial", phytomedicine (2009), doi:10.1016/J. phymed. 2009.09.003 describes a clinical trial of a rose hip containing both rose hip shells and seeds, wherein the rheumatoid arthritis patients are treated with a daily dose of 5 g of rose hip powder similar to the above used product containing both rose hip shells and seeds.

In WO 03/043613 A1 compounds may be extracted by organic solvents and a bioguided fractionation procedure of rose hips shells. These extracts were shown to contain the highly active anti-inflammatory agent GOPO (which is a registered trademark). The action of this compound was shown to be alleviating chemiluminescence of polymorphnuclear leucocytes and chemotaxis of mononuclear leucocytes. An aqueous formulation containing the highly anti-inflammatory agent was suggested.

In WO 2008/003314 A1 another method of producing a concentrate, e.g. of GOPO, in particular from a rose hip material is disclosed.

In WO 2009/080778 A2 a composition having a low concentration of GOPO is based on an ethanolic extract of rose hip shells in combination with another chondroprotective product such as a collagen hydrolysate, glucosamine, and/or chondroitin sulphate.

The known rose hip containing compositions, concentrates or extracts are used in prophylaxis and or alleviating symptoms of inflammatory diseases, e.g. joint diseases such as arthritis and/or osteo arthritis.

The Rose hip seeds of *Rosa Canina* contain about 7% (by weight) of oils. This results in complicated and expensive methods for extracting the oils from the rose hip seeds having varying yields as disclosed in Szentmihalyi et al. Further, the extraction of the oils renders it likely that other active substances, especially substances being insoluble in oils, are excluded from the product. The oils present in the rose hip seeds, may contribute to the anti-inflammatory effect of the rose hip seeds but are unlikely to be entirely responsible for the anti-inflammatory effect of the rose hip seeds especially due to the relatively low content of the oils in the rose hip seeds.

Even though the known rose hip compositions may be useful as a natural anti-inflammatory ingredient during treatment of patients suffering from these diseases, the daily dose needed may be quite large, e.g. 45 g rose hip powder as disclosed in U.S. Pat. No. 6,024,960 A or 5 g (10 capsules) daily dose of rose hips as described by Winther et al and Willich et al. The patients will be likely to find the daily dose rather large, and may, in some instances, have problems swallowing this rather large amount of powder or capsules.

A consequence may be that the patient ceases to use the rose hip product because the effective daily dose is "too bulky".

Thus, there is still a need for alternative Rose hip products, especially products which may increase the anti-inflammatory effect of the Rose hip compositions, or decrease the volume of the daily dose and/or which may lower the effective daily dose of rose hip needed to obtain an anti-inflammatory effect, in particular in alleviation of symptoms of joint diseases, such as arthritis and/or osteo arthritis.

SUMMARY OF THE INVENTION

The object of the present invention is therefore to provide a composition, which may increase the anti-inflammatory effect of the daily dose of the Rose hip compositions and/or reduce the volume of an effective daily dose and/or reduce the effective daily dose of a rose hip composition.

This is achieved by a composition which comprises rose hip flesh or rose hips including their naturally occurring amount of seeds or a concentrate of rose hip flesh or rose hips including the naturally occurring amount of seeds, wherein the composition is enriched with a dried powdered material of rose hip seeds.

Seeds from the rose hips have shown anti-inflammatory effects and antioxidant effects (which are indicated as inhibition of chemotaxis and of chemiluminescence in in-vitro assays of polymorphnouclear leukocytes, PMN), which surprisingly appears stronger than the flesh of the rose hips alone or a composition containing rose hips including the naturally occurring amount of seeds. Similarly, it appears that the anti-inflammatory effect, when chemotaxis of neutrophile leucocytes is used as the model, in in-vivo tests decreases with decreasing amounts of Rose hips seeds in the Rose hip product. The stronger effect of compositions having an increased content of rose hip seeds therefore seems to arise from substances present only in the seeds of rose hips. The strong anti-inflammatory effect, which is indicated by chemotaxis inhibition, further implies that rose hip seeds are useful in the treatment or prevention or alleviation of inflammatory diseases, especially inflammatory joint diseases, such as arthritis and osteoarthritis.

Further, these results also imply that the necessary daily dose of rose hip products may be significantly reduced when using a product consisting of rose hip seeds.

The composition enriched with rose hip seeds also act stronger with regard to the anti-oxidant properties when compared to a rose hip product having a seeds content corresponding to the normal amount of seeds in rose hips in in-vitro assays when using chemiluminescence as the model for antioxidant activity.

When providing the Rose hip seeds in a dried powdered form, all the active compounds present in the rose hip seeds are present in their natural environment. In this form, the active compounds are naturally protected from degradation, e.g. oxidation of unsaturated fatty acids, vitamins etc. present in the Rose hip seeds, in relation to compounds or compositions, which are isolated, extracted or otherwise obtained in a more or less pure form from the rose hip seeds. The rose hip seeds material is therefore believed to demonstrate improved stability when compared to the isolated extracts, compounds or compositions. Furthermore, the naturally occurring fibers and other constituents of the rose hip seeds provide an entirely natural "slow release formulation" for the anti-oxidants and anti-inflammatory active substances present in the rose hip seeds.

The invention is a composition containing a powder or a concentrate of rose hip flesh alone or of rose hips, including their naturally occurring amount of seeds, where the anti-inflammatory effect as well as the anti-oxidative effect may be increased by enriching these compositions with a rose hip seeds material. A similar effect is believed to arise when a conventional composition comprising rose hip flesh or a concentrate hereof is enriched with the rose hip seeds product, i.e. reducing the daily dose when compared to the rose hip flesh product alone.

The rose hip seeds product is preferably added to the rose hip containing composition, resulting in a composition containing at least 50% by weight, preferably 50-85% and more preferred 60-80% of the rose hip seeds material (in weight % of the resulting composition of rose hip seeds and rose hip flesh).

The unit dosage is presented in the form of a powder, e.g. in sachets. The powder may also be incorporated into capsules, tablets, caplets, lozenges or in a suspension. The composition is preferably in the form of a daily dose applicable for acute administration of about 0.015-0.57 g/kg bodyweight preferably 0.07-0.285 g/kg bodyweight and most preferred 0.115-0.171 g/kg bodyweight in unitary or multiple doses. The daily dose for acute administration to humans is therefore 1-40 g, preferably 5-20 g and more preferred 8-12 g rose hip seeds in daily unitary or multiple doses.

The composition may also be in the form of a daily dose applicable for prophylactic administration of about 0.015-0.07 g/kg bodyweight preferably 0.015-0.05 g/kg bodyweight and most preferred 0.021-0.036 g/kg bodyweight in unitary or multiple doses.

The daily dose for prophylactic administration to humans is therefore 1-5 g, preferably 1-3.5 g and more preferred 1.5-2.5 g of rose hip seeds in daily unitary or multiple doses.

As described further below, the rose hip concentrate or the rose hip material of the composition as well as the Rose hip seeds are obtained from Rose hips of plants selected from the group consisting of *Rosa canina* ("dog rose hip"), *Rosa gallica, Rosa condita, Rosa rugosa, Rosa hugonis, Rosa nitida, Rosa pendulina, Rosa pimpinellifolia*, and *Rosa sericea*. It is preferred that the rose hip concentrate or the rose hip material of the composition as well as the Rose hip seeds are obtained from Rose hips of *Rosa Canina*, preferably from *Rosa Canina* L and more preferred *Rosa Canina* L (Lito).

The Rose hip composition being enriched with the rose hip seeds may also be solid or liquid concentrates of Rose hips flesh or the Rose hips including their naturally occurring amount of seeds which may be treated for obtaining an increased content of the ingredients such as GOPO, vitamins etc. as well as other potentially active ingredients.

The object of the present invention is also to provide a method for producing a rose hip seeds composition according to the invention as disclosed in claim 9, said method comprising fracturing a plurality of rose-hips into pieces; separating the seeds from a flesh portion of the rose-hips and from other matter; drying the rose-hip seeds at temperatures below 50°

C. and preferably below 40° C., to a water content of about 5%; grinding the dried seeds of the rose-hips to produce a powder; and providing the powder in a physiologically acceptable form.

This method provides a gentle treatment to the rose hip seeds and preserves a substantial amount of active compounds present in the rose hip seeds, including compounds which are susceptible to thermal degradation, e.g. unsaturated fatty acids, vitamins etc. Furthermore, by preserving the active compounds in their natural environment, the rose hip seeds material probably demonstrates improved stability when comparing to degradation of compounds present in extracts or concentrates such as oils and other compounds, especially presently unknown antioxidants and/or compounds having anti-inflammatory effect. The natural amount of dietary fibers present in the rose hip seeds is also preserved, which may contribute intestinal health in addition to the anti-inflammatory effect of the Rose hip seeds naturally occurring fibers and other constituents of the rose hip seeds. The fibers and other constituents of the rose hip seeds also provide a natural "slow release formulation" for the anti-oxidants and anti-inflammatory active substances present in the rose hip seeds.

As described further below, it may be expedient subjecting the rose hips to freezing for storage prior to fracturing the rose hips. It may also be expedient to separate the rose hip seeds from the flesh while the chopped rose hips are frozen, since the frozen rose hips act as if they were dried and are easily separated, e.g. by sifting. Alternatively, the frozen rose hips may be subjected to a gentle wet grinding. The rose hip flesh is then thawed and crushed during grinding and a mixture of rose hip seeds, hairs and semi liquid pulp of the flesh is produced. The seeds, including the hairs, can be easily removed from the pulp by sifting and the hairs may be removed from the seeds after drying of the rose hip seeds. It is advantageous to separate the Rose hip seeds from the flesh prior to the drying step, since the flesh contains more water than the rose hips and thus requires a prolonged drying. Separating the flesh from the seeds prior to drying shortens the drying time for the rose hip seeds substantially, leading to a more gentle drying treatment of the rose hip seeds and a reduced energy consumption.

A further possibility is separating the rose hip seeds from the flesh and other matter after the drying step.

The rose hip seeds material is added to a composition or a concentrate containing dried rose hip flesh or dried rose hips including the naturally occurring amount of seeds, whereby a reduction in the volume of the effective daily dose of the rose hip composition may be achieved.

The Rose hip seeds enriched composition is suitable for use for the preparation of a medicament for the treatment, alleviation or prophylaxis of inflammatory conditions in a mammal.

The rose hip seeds product may be used when treating and alleviating symptoms in mammals of inflammatory conditions, such as, but not limited to hepatitis, meningitis, rheumatoid arthritis, inflammatory bowl diseases, such as Crohns disease, allergic syndromes, diabetes, congestive heart disease, psoriatic, reactive or osteoarthritis or other arthritides or joint diseases, multiple sclerosis, atherosclerosis, sepsis/septic shock, dermal inflammation, graft rejection, and inflammation secondary to chemotherapy or radiotherapy of neoplastic diseases.

It is preferred to use the rose hip seed product in preventing and/or treating and/or alleviating the symptoms, e.g. pain and joint stiffness, associated with joint diseases, such as arthritis, osteoarthritis, rheumatoid arthritis etc.

The term "mammal" includes larger animals, such as humans or domestic farm animals such as horses, dogs, cats, sheep, pigs or cattle.

In addition, the Rose hip seeds enriched composition is used for the treatment, alleviation or prophylaxis of inflammatory conditions in a mammal

BRIEF DESCRIPTION OF THE DRAWINGS

The invention will now be described further with reference to the drawings in which.

DETAILED DESCRIPTION OF THE INVENTION

Figure 1:
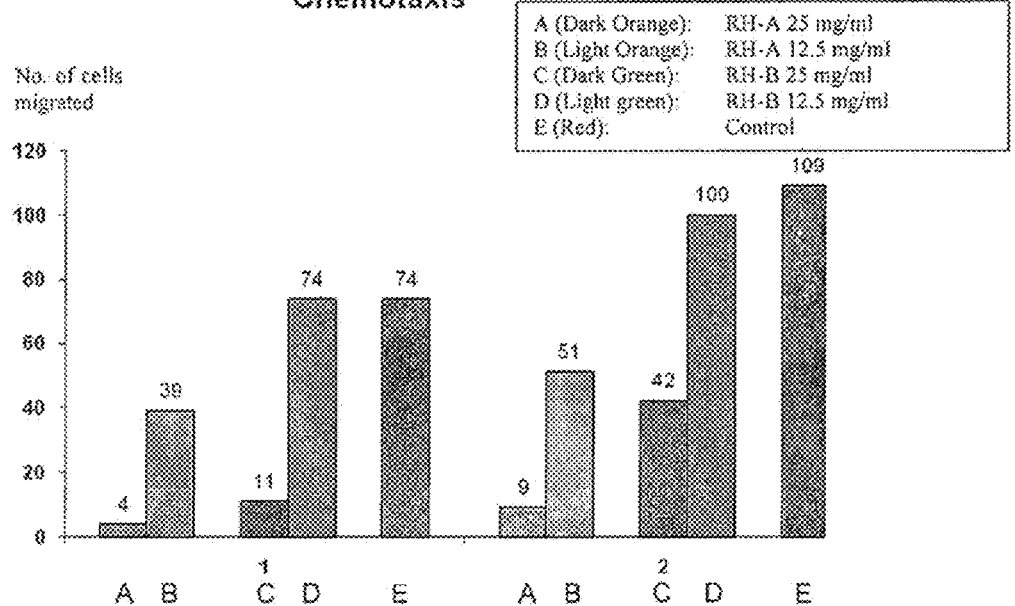
FIG. 1 illustrate the results of example 1a in which the anti-inflammatory effect of Rose hip seeds is investigated by comparing the results inhibition of chemotaxis of inflammatory cells of human blood under influence of a first rose hip composition (RH-A) having approximately 50% (by weight) of rose hip seeds and a second composition (RH-B) having the content of seeds reduced in relation to RH-A.

The Composition:

The rose hip flesh or rose hips including their naturally occurring amount of seeds or a concentrate of rose hip flesh or rose hips including the naturally occurring amount of seeds as well as the rose hip seeds used for enriching the rose hip composition are preferably obtained from rose hips of wild type rose bushes, in particular the rose hip is selected from the group consisting of *Rosa canina* ("dog rose hip"), *Rosa gallica, Rosa condita, Rosa rugosa, Rosa hugonis, Rosa nitida, Rosa pendulina, Rosa pimpinellifolia*, and *Rosa sericea.*

It is preferred to use rose hips material and rose hip seeds of *Rosa canina*, including *Rosa canina* L. The preferred subtype is *Rosa canina* Lito.

After the rose hips are harvested, the hips may be frozen for storage until being further processed. The fresh or frozen rose hips may be chopped into pieces before further processing. In any event, the next step is to dry the chopped Rose hips to a water content of about 5% by weight. It is essential that the drying is conducted in a manner which preserves any of the vitamins present in the rose hip seeds and possibly the content of any presently unknown active compounds present in the seeds of the rose hips. Preferably, drying is conducted at a temperature below 50° C., preferably below 40° C., with air and avoiding sunlight. It may be beneficial to utilize low pressure as well as low temperature to facilitate drying.

The dried, chopped rose hips then pass through a separation step to separate the nuts/seeds and the dried flesh into two fractions while removing hairs, and other extraneous matter that may have accompanied the rose hips during harvesting. Alternatively, the seeds are separated from the flesh prior to the drying step, while removing hairs and other extraneous matter may be performed simultaneously with separation the step or, alternatively, after drying. For example, the rose hip seeds can be separated from the flesh while the chopped rose hips are frozen. When the Rose hips are frozen they act similarly to dried rose hip seeds and the rose hips are easily separated from the flesh, e.g. by sifting.

The frozen rose hips may, alternatively, be subjected to a gentle wet grinding step, in which the rose hip flesh is thawed and crushed during grinding, following which a mixture of rose hip seeds, hairs and semi liquid pulp of the flesh is produced. The seeds, including the hairs, can be easily removed from the pulp by sifting and the hairs may be removed from the seeds after drying of the rose hip seeds e.g. by suction. It is advantageous to separate the rose hip seeds from the flesh prior to the drying step, since the flesh contains more water than the rose hips and thus requires a prolonged drying. Separating the flesh from the seeds prior to drying shortens the drying time for the rose hip seeds substantially, leading to a more gentle and uniform drying treatment of the rose hip seeds and a reduced energy consumption.

The dried rose hip seeds are then crushed in a grinding mill. A powder or granular material may be obtained having a particle size of below 1 mm, with about 0.1-0.5 mm preferred. For ease in illustration, the term "powder" will be used to cover the full spectrum of the dried rose hip seeds in whatever solid form it takes. It will be understood, of course, that the powder may be presented and used as a suspension.

Preferably, the rose hip seeds enriched composition may be pelletized or placed in capsules, optionally with a physiologically acceptable carrier for formulation into unit dosages. Alternatively, the unit dosage a powdered rose hip seeds enriched composition may be put into sachets.

The dried and finely ground rose hip seeds material according to the invention is mixed with a concentrate of Rose hips, optionally including their natural amount of seeds or a rose hip composition comprising dried ground flesh of rose hips, optionally including their natural amount of seeds, in order to obtain a rose hips seeds enriched formulation according to the invention. The total amount of rose hip seeds present in the composition enriched with rose hip seeds is preferably at least 50% by weight, preferably 50-85% and more preferred 60-80%.

The Rose hip composition being enriched with the rose hip seeds may also be solid or liquid concentrates of Rose hips flesh or the Rose hips including their naturally occurring amount of seeds which may be treated for obtaining an increased content of the ingredients such as GOPO, vitamins etc. as well as other potentially active ingredients. Examples of suitable solid concentrates of Rose hip material are disclosed in U.S. Pat. No. 6,024,960 A or WO 2008/003314 A1 and an example of a suitable liquid concentrate of a rose hip material is disclosed in WO 2003/043613 A1, each of these documents hereby being incorporated by reference. Although a solid concentrate of Rose hip, e.g. including naturally occurring amount of seeds is preferred, it is also possible to use a liquid concentrate. It is to be understood, that when a liquid concentrate is enriched with the Rose hip seeds material, the result is a suspension of the solid Rose hip seed material in the liquid concentrate or a paste, depending on the amount of Rose hip seed material being added to the composition.

As mentioned above, the composition according to the invention can be formulated for delivery via various routes of administration. Administration may proceed by oral, buccal, parenteral, topical, rectal, transdermal or intranasal administration, though oral administration is preferred for ease of use.

In either instance, the Rose hip seed enriched composition according to the invention may be manufactured into tablets, capsules, caplets, lozenges, suspensions, pastes, enteral formulations or be incorporated into slow release carriers, where the solid composition as described above, is particularly suitable for being incorporated into tablets, capsules, lozenges, caplets and/or slow release carriers.

The Rose hip seed composition may further comprise conventional physiologically acceptable carriers and/or adjuvants. Examples of other physiologically acceptable carriers would also include oils, oil emulsions, alcohol, etc.

Furthermore, the Rose hip seed composition may also contain one or more other additional ingredients, which are used in the prophylaxis and/or treatment of e.g. joint diseases or other inflammatory conditions than those mentioned above, e.g. glucosamine, turmeric and/or ginger root extracts and optionally Vitamin D in combination with Calcium etc.

The present invention is presently believed to be particularly suitable for the treatment of arthritis and/or osteo arthritis.

The term "mammal" is intended to include larger mammals such as humans as well as domestic or farm animals such as dogs, cats, horses, sheep, pigs, cattle, etc. Among these mammals, humans are particularly interesting subjects to benefit from the invention.

EXPERIMENTAL RESULTS

A powdered rose hip product ("RH-A") based on the combination of dried rose hip flesh powder and dried rose hip seeds powder was produced according to the method of the invention and having a total amount of approximately 50% (by weight) of Rose hip seeds was provided by Hyben Vital ApS.

A second and commercially available powdered rose hip product ("RH-B") was also produced as described for the present invention, with the exception that the rose hip powder contains the natural amount of rose hip seeds, which is approximately 30% (by weight). RH-B was also was provided by Hyben Vital ApS.

Example 1

Comparison of the Anti-Inflammatory and the Anti-Oxidant Activity of RH-A with RH-B These assays are based on two biological functions of the inflammatory cells from human blood. One assay is called chemotaxis and measures the migration of cells to the inflammatory sites/foci. Inhibition of this function by any product indicates the anti-inflammatory property of the product tested. The other assay is called chemiluminescence, which measures the generation of reactive oxygen radicals by these cells also called oxidative burst response. Inhibition of chemiluminescence indicates the anti-oxidant property of the product tested.

Cells

Polymorphouclear leukocytes (PMNs) are isolated from the peripheral blood of healthy subjects, suspended in appropriate culture medium and used for the biological activity assays.

Example Ia

Chemotaxis

Chemotaxis assay is performed using a modified Boyden chamber technique. The purified PMNs are pre-incubated with different concentrations of the two different rosehip powder products or control medium for 30 min at 37° C. Following pre-incubation, the chemotaxis of the cells towards the chemotactic factor zymosan activated serum (ZAS), which contains the biologically active chemoattractant C5a, are tested. The number of migrated cells is counted by a computer-assisted image analysis system. The inhibition of chemotaxis is then determined as the percentage of the cell response in control culture medium.

Example 1b

Chemiluminescence

Chemiluminescence assay is used as a measure of oxygen radical generation by activated PMNs. PMNs are pre-incubated with different concentrations of the two different rosehip powder products or control medium for 30 min at 37° C. and then stimulated with opsonized zymosan. The oxidative burst response of the activated cells is then measured by a luminometer as counts per minute (CPM). The inhibition of chemiluminescence is then determined as the percentage of the cell response in control culture medium.

The assays of 1a and 1b were both repeated twice.
Results
The results in table 1 are shown as percentage inhibition of the cell response.

TABLE 1

| RH-A | Chemotaxis | Chemilumi nescense | RH-B | Chemotaxis | Chemilumi nescense |
|---|---|---|---|---|---|
| 25 mg/ml | 94% | 80% | 25 mg/ml | 63% | 61% |
| 12.5 mg/ml | 50% | 61% | 12.5 mg/ml | 5% | 36% |

The results in FIG. 1 show the comparison of the anti-inflammatory activity using two different concentrations of RH-A and RH-B rosehip powder in two separate runs.

Figure 2:
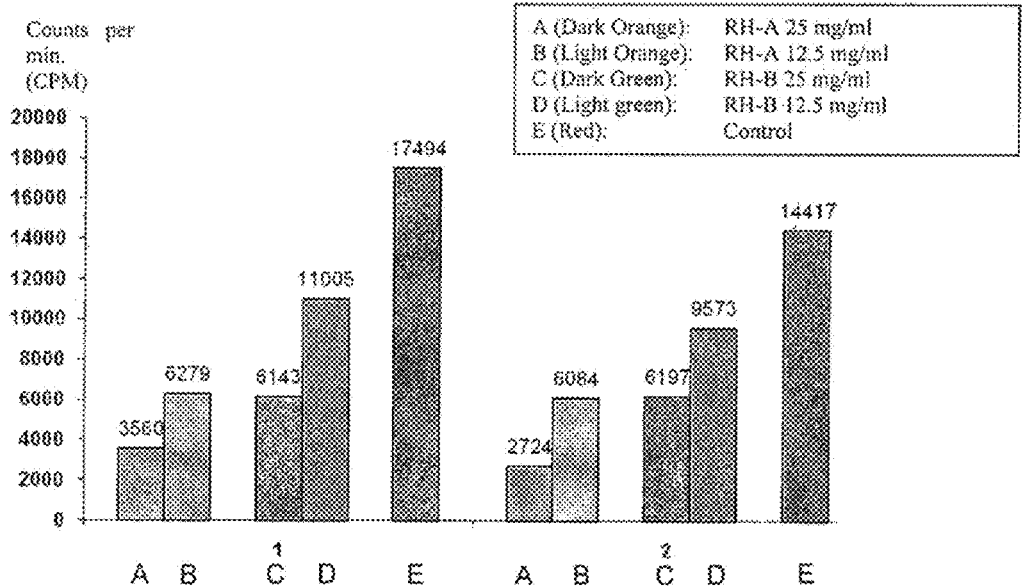
FIG. 2 illustrate the results of example 1b in which the anti-oxidant effect of Rose hip seeds is investigated by comparing the results inhibition of chemiluminescence of inflammatory cells of human blood under influence of a first rose hip composition (RH-A) having approximately 50% (by weight) of rose hip seeds and a second composition (RH-B) having the content of seeds reduced in relation to RH-A.

The results in FIG. 2 show the comparison of the anti-oxidant activity using two different concentrations of RH-A and RH-B rosehip powder in two separate runs.

Conclusions

The results presented show that both RH-A and RH-B rose hip powder exhibit anti-inflammatory as well as anti-oxidant activity in a dose-dependent manner. It appears that the activity of RH-A is higher than RH-B in these two assays.

Since the two rose hip products, RH-A and RH-B, only differ from each other by the increased content of rose hip seeds in RH-A, one can conclude, that the stronger effect of RH-A probably arises from substances present in the rose hip seeds of RH-A. The strong anti-inflammatory effect, which is indicated by the chemotaxis inhibition, further implies that rose hip seeds are useful in the treatment or prevention or alleviation of inflammatory diseases, especially inflammatory joint diseases, such as arthritis and osteoarthritis.

Further, these results also imply that the necessary dose of rose hip products may be reduced when using a product consisting of or containing a majority of rose hip seeds, since the lower concentration (12.5 mg/ml) of RH-A (which comprises 50% rose hip seeds) has approximately the same effect of inhibition of chemotaxis and chemiluminescence as the high concentration (25 mg/ml) of RH-B with the low content of rose hip seeds.

An increase in content of rose hip seeds (see results of chemiluminescence from RH-A compared to RH-B) also shows increased inhibition of chemiluminescence, which indicates the anti-oxidant property of the product having a high content of seeds (RH-A) is stronger than the product having a lower content of rose hip seeds (RH-B).

Example 2

Initially, blood samples of 12 healthy trotting horses were collected. Within 2 hours after the blood samples were taken, neutrophile leucocytes were isolated from each of the blood samples and chemotaxis was determined using the same test design as described for the in vitro tests in example 1a, but without pre incubation of the cells in a Rose hip extract.

The results of the initial values for chemotaxis of neutrophile leucocytes (i.e. the number of migrated cells) in the horses is 30.4+/−14 which represents the chemotaxis in horses not subjected to treatment with the Rose hip seeds containing products.

The horses are then treated with a powder of RH-A for a period of 3 months, which was sprinkled over the daily fodder. The horses were given a daily dose of 0.3-0.5 g RH-A/kg bodyweight.

After 3 months of treatment with the RH-A product a second blood sample was taken from the horses. The blood sample was treated similarly to the initial blood test and chemotaxis was determined using the same method. Chemotaxis of the neutrophile leucocytes after 3 months of treatment was 9.0+/−13.5. The inhibition of chemotaxis of neutrophile leucocytes is approximately 71% after 3 months of treatment with RH-A.

The result of inhibition of chemotaxis of neutrophile leucocytes in horses after treatment with RH-A in percentage of the initial value is shown in table 2.

TABLE 2

|  | Neutrophile leucocytes in horses | Neutrophile leucocytes in dogs |
|---|---|---|
| Rose hip product | RH-A | RH-B |
| Daily dose | 0.3-0.5 g/kg bodyweight | 0.32 g/kg bodyweight |
| Chemotaxis Inhibition | 71.3% | −2.7% |

Similarly, blood samples of 12 healthy greyhounds were collected. Within 2 hours after the blood samples were taken, neutrophile leucocytes were isolated from each of the blood samples and chemotaxis was determined using the same test design as described for the in vitro tests as above mentioned.

The initial mean value of chemotaxis of neutrophile leucocytes (i.e. the number of migrated cells) in dogs was 122.1+/−47.8 which represents the chemotaxis in dogs not subjected to treatment with the Rose hip seeds containing products.

The greyhounds are then treated with a powder of RH-B for a period of 3 months, which was sprinkled over the daily fodder. The animals were given a daily dose of 0.32 g RH-B/kg bodyweight.

After 3 months of treatment with the RH-B product a second blood sample was taken from the dogs. The blood sample was treated similarly to the initial blood test and chemotaxis was determined using the same method. After 3 months of treatment with RH-B of the dogs, the mean value of chemotaxis of the neutrophile leucocytes extracted from blood of RH-B treated dogs was 125.4+/−49.5 and represents a small increase in chemotaxis of 2.7% rather than a reduction in chemotaxis.

The result of inhibition of chemotaxis of neutrophile leucocytes in dogs after treatment with RH-B in percentage of the initial value is also shown in table 2.

Conclusions

The initial values of chemotaxis in the horses and the dogs represent the chemotaxis in animals not subjected to treatment with the Rose hip seeds containing products. The results of the percentage of inhibition of chemotaxis after 3 months of treatment with the Rose hips seeds containing products are shown in table 2 and arise from the reduction in chemotaxis after 3 months in relation to chemotaxis in the animals prior to treatment with the Rose hip seeds containing products.

Even though RH-A and RH-B was tested in horses and dogs, the neutrophile leucocytes of horses and dogs normally act similarly and the results should therefore be comparable.

The value of inhibition of chemotaxis is 71.3% after treatment of the horses with RH-A, demonstrates high significance (p<0.004).

The corresponding value of inhibition of chemotaxis is 2.7% after treatment of the dogs with RH-B (p>0.742) which is not insignificant.

Thus, the results clearly demonstrate that increasing the amount of rose hips seeds in the Rose hip product leads to an increased anti-inflammatory effect, when chemotaxis is used as a model for the anti-inflammatory effect.

The invention claimed is:

1. A composition which comprises a rose hip ingredient selected from the group consisting of rose hip flesh, rose hips including their naturally occurring amount of seeds, a concentrate of rose hip flesh, and a concentrate of rose hips including the naturally occurring amount of seeds, and, an enrichment ingredient consisting of a dried powdered rose hip seeds raw plant material.

2. The composition according to claim 1 wherein the dried powdered rose hip seeds raw plant material is added to the rose hip ingredient such that the total amount of rose hip seeds present in the composition is at least 50%.

3. The composition according to claim 1 wherein the dried powdered rose hip seeds raw plant material is added to the rose hip ingredient such that the total amount of rose hip seeds present in the composition is in a range of 50% to 85%.

4. The composition according to claim 1 wherein the dried powdered rose hip seeds raw plant material is added to the rose hip ingredient such that the total amount of rose hip seeds present in the composition is in a range of 60% to 80%.

5. The composition according to claim 1, wherein the composition is in a unit dosage form.

6. The composition according to claim 1 wherein the composition is in the form of a powder, the powder optionally incorporated into capsules, tablets, caplets, lozenges or a suspension.

7. The composition according to claim 1 wherein the composition is in a daily dose form adapted to administer about 0.015-0.57 g/kg bodyweight, in a single dose or in multiple doses.

8. The composition according to claim 1 wherein the composition is in a daily dose form adapted to administer about 0.07-0.285 g/kg bodyweight, in a single dose or in multiple doses.

9. The composition according to claim 1 wherein the composition is in a daily dose form adapted to administer about 0.115-0.171 g/kg bodyweight, in a single dose or in multiple doses.

10. The composition according to claim 1 wherein the composition is in the form of a prophylactic daily dose adapted to administer about 0.015-0.07 g/kg bodyweight, in a single dose or in multiple doses.

11. The composition according to claim 1 wherein the composition is in the form of a prophylactic daily dose adapted to administer about 0.015-0.05 g/kg bodyweight, in a single dose or in multiple doses.

12. The composition according to claim 1 wherein the composition is in the form of a prophylactic daily dose adapted to administer about 0.021-0.036 g/kg bodyweight, in a single dose or in multiple doses.

13. The composition according to claim 1 wherein the rose hip ingredient and the dried powdered rose hip seeds raw plant material are obtained from rose hips of plants selected from the group consisting of *Rosa canina*, *Rosa gallica*, *Rosa condita*, *Rosa rugosa*, *Rosa hugonis*, *Rosa nitida*, *Rosa pendulina*, *Rosa pimpinellifolia*, and *Rosa sericea*.

14. The composition according to claim 1 wherein the rose hip ingredient and the dried powdered rose hip seeds raw plant material are obtained from rose hips selected from the group consisting of *Rosa Canina*, *Rosa Canina* L and *Rosa Canina* L (Lito).

15. A method for treating, alleviating the symptoms of or reducing the incidence of an inflammatory condition in a mammal comprising administering to said mammal an effective amount of a rose hip seed enriched composition containing a rose hip ingredient selected from the group consisting of rose hip flesh, rose hips including their naturally occurring amount of seeds, a concentrate of rose hip flesh, and a concentrate of rose hips including the naturally occurring amount of seeds, and, an enrichment ingredient consisting of a dried powdered rose hip seeds raw plant material.

16. The method according to claim 15, wherein the inflammatory condition is selected from hepatitis, meningitis, rheumatoid arthritis, inflammatory bowel diseases, Crohns disease, allergic syndromes, diabetes, congestive heart disease, psoriatic, reactive or osteo-arthritis; other arthritides, joint diseases, multiple sclerosis, atherosclerosis, sepsis/septic shock, dermal inflammation, graft rejection, and inflammation secondary to chemotherapy or radiotherapy of neoplastic diseases.

17. The method according to claim 15, wherein the inflammatory condition is a joint disease.

18. The method according to claim 15, wherein the inflammatory condition is arthritis.

19. The method according to claim 15, wherein the inflammatory condition is osteo-arthritis.

20. The method according to claim 15, wherein the inflammatory condition is rheumatoid arthritis.

21. The method according to claim 15, wherein the mammal is selected from the group consisting of humans, horses, dogs, cats, sheep, pigs and cattle.

22. The method according to claim 15, wherein the rose hip seeds enriched composition contains a total amount of at least 50% rose hip seeds.

23. The method according to claim 15, wherein the rose hip seeds enriched composition contains a total amount of rose hip seeds in a range of 50% to 85%.

24. The method according to claim 15, wherein the rose hip seeds enriched composition contains a total amount of rose hip seeds in a range of 60% to 80%.

25. The method according to claim 15 further comprising providing the rose hip seeds enriched composition in a unit dosage form.

26. The method according to claim 15 further comprising providing the rose hip seeds enriched composition in the form of a powder, and, incorporating the powder into capsules, tablets, caplets, lozenges or a suspension.

27. The method according to claim 15, wherein the administering step comprises administering a daily dose of the rose hip seeds enriched composition, which comprises 0.015-0.57 g/kg bodyweight, administered in a single dose or in multiple doses.

28. The method according to claim 15 wherein the administering step comprises administering a daily dose of the rose hip seeds enriched composition which comprises 0.07-0.285 g/kg bodyweight, administered in a single dose or in multiple doses.

29. The method according to claim 15 wherein the administering step comprises administering a daily dose of the rose hip seeds enriched composition which comprises 0.115-0.171 g/kg bodyweight, administered in a single dose or in multiple doses.

30. The method according to claim 15 wherein the administering step comprises administering a daily dose of the rose hip seeds enriched composition which comprises 0.015-0.07 g/kg bodyweight, administered in a single dose or in multiple doses.

31. The method according to claim 15 wherein the administering step comprises administering a prophylactic daily dose of the rose hip seeds enriched composition which comprises 0.015-0.05 g/kg bodyweight, administered in a single dose or in multiple doses.

32. The method according to claim 15 wherein the administering step comprises administering a prophylactic daily dose of the rose hip seeds enriched composition which comprises 0.021-0.036 g/kg bodyweight, administered in a single dose or in multiple doses.

33. The method according to claim 15 wherein the rose hip ingredient and the dried powdered rose hip seeds raw plant material are obtained from rose hips of plants selected from the group consisting of *Rosa canina, Rosa gallica, Rosa condita, Rosa rugosa, Rosa hugonis, Rosa nitida, Rosa pendulina, Rosa pimpinellifolia*, and *Rosa sericea.*

34. The method according to claim 15 wherein the rose hip ingredient and the dried powdered rose hip seeds raw plant material are obtained from rose hips selected from the group consisting of *Rosa Canina, Rosa Canina* L and *Rosa Canina* L (Lito).

* * * * *